US009814532B2

(12) United States Patent
Bell et al.

(10) Patent No.: US 9,814,532 B2
(45) Date of Patent: Nov. 14, 2017

(54) SYSTEM AND METHOD FOR ESTIMATING THE SPATIAL POSITION OF A TOOL WITHIN AN OBJECT

(71) Applicant: UNIVERSITAT BERN, Bern (CH)

(72) Inventors: Brett J. Bell, Schliern (CH); Stefan Weber, Boll (CH); Tom Williamson, Bern (CH)

(73) Assignee: UNIVERSITAT BERN, Bern (CH)

( * ) Notice: Subject to any disclaimer, the term of this patent is extended or adjusted under 35 U.S.C. 154(b) by 538 days.

(21) Appl. No.: 14/402,323

(22) PCT Filed: May 21, 2013

(86) PCT No.: PCT/EP2013/060389
§ 371 (c)(1),
(2) Date: Nov. 20, 2014

(87) PCT Pub. No.: WO2013/174801
PCT Pub. Date: Nov. 28, 2013

(65) Prior Publication Data
US 2015/0157419 A1    Jun. 11, 2015

(30) Foreign Application Priority Data

May 21, 2012    (EP) .................................... 12168772

(51) Int. Cl.
*A61B 19/00*    (2006.01)
*A61B 34/00*    (2016.01)
(Continued)

(52) U.S. Cl.
CPC .............. *A61B 19/56* (2013.01); *A61B 34/10* (2016.02); *A61B 34/25* (2016.02); *A61B 34/30* (2016.02);
(Continued)

(58) Field of Classification Search
CPC ......... A61B 34/20; A61B 34/30; A61B 19/56; A61B 34/10; A61B 34/25; G06T 7/74
See application file for complete search history.

(56) References Cited

U.S. PATENT DOCUMENTS 6,718,196 B1    4/2004    Mah et al.
6,887,247 B1 *  5/2005    Couture ............. A61B 17/1703
                                                  408/72 R
(Continued)

FOREIGN PATENT DOCUMENTS

DE    102005029002    12/2006
DE    102008013429    10/2009
(Continued)

*Primary Examiner* — Timothy Waggoner
(74) *Attorney, Agent, or Firm* — JMB Davis Ben-David

(57) ABSTRACT

The invention relates to a system for estimating the spatial position (pose) of a tool (2) within an object (1), particularly in the form of a human bone that is to be machined with said tool, comprising: a sensor (21) being designed to be coupled to said tool (2), which sensor (21) is further designed to generate an sensor output signal (31) upon machining of said object (1) along an actual trajectory (30), which sensor output signal (31) depends on a material property of said object along said actual trajectory (30), an analyzing means being designed to determine a correlation between said sensor output signal (31) upon machining said object (1) and a plurality of pre-determined candidate output signals (42), each candidate output signal (42) being generated in beforehand using said material property along an associated model trajectory (40) in a model of said object (1), and wherein said analyzing means is designed to estimate a spatial position of the tool (2) within the object (1) using the model trajectory (40) whose associated candidate output signal (42) has the highest correlation with the sensor output signal (31), for instance. The invention further relates to a method for estimating the pose of the tool (2), as well as a computer program product.

15 Claims, 4 Drawing Sheets

(51) Int. Cl.
*A61B 34/30* (2016.01)
*G06T 7/73* (2017.01)
*A61B 34/10* (2016.01)
*A61B 90/00* (2016.01)

(52) U.S. Cl.
CPC .......... *G06T 7/74* (2017.01); *A61B 2034/104* (2016.02); *A61B 2034/107* (2016.02); *A61B 2090/065* (2016.02); *G06T 2207/10072* (2013.01); *G06T 2207/30164* (2013.01); *G06T 2207/30196* (2013.01); *G06T 2207/30241* (2013.01)

(56) References Cited

U.S. PATENT DOCUMENTS

| | | | |
|---|---|---|---|
| 7,782,709 B2 * | 8/2010 | Esmersoy | E21B 21/08 |
| | | | 324/323 |
| 2004/0010190 A1 | 1/2004 | Shahidi | |
| 2007/0181139 A1 | 8/2007 | Hauck | |
| 2007/0225787 A1 | 9/2007 | Simaan et al. | |
| 2011/0112397 A1 | 5/2011 | Shen et al. | |
| 2011/0306985 A1 * | 12/2011 | Inoue | G06T 15/08 |
| | | | 606/130 |

FOREIGN PATENT DOCUMENTS

| | | |
|---|---|---|
| WO | WO2009092164 | 7/2009 |
| WO | WO2010147972 | 12/2010 |

* cited by examiner

SYSTEM AND METHOD FOR ESTIMATING THE SPATIAL POSITION OF A TOOL WITHIN AN OBJECT

CROSS-REFERENCE TO RELATED APPLICATIONS

This is the U.S. National Stage of International Application No. PCT/EP2013/060389, filed May 21, 2013, which was published in English under PCT Article 21(2), which in turn claims the benefit of EP Patent Application No. 12168772.7, filed May 21, 2012.

SPECIFICATION

The invention relates to a system for estimating the spatial position (pose) of a tool within an object, particularly in the form of a human bone (e.g. the mastoid process of the temporal bone of a human skull) that is to be machined with said tool. Further, the invention relates to a method for estimating the spatial position of a tool within an object.

Currently available machining systems such as computer numerically controlled machines, robots and the like utilize position sensors to estimate a tool pose relative to the coordinate system of the object being manipulated. Typically, position sensing is achieved by means of digital encoders, stereo-optic cameras, and laser range scanners among others.

In certain circumstances, a digital model of the object being manipulated is available and used to define actions of the tool to the object. For instance in surgery, a three-dimensional scan of a bone is used to define the optimal position for a cavity to be machined into the bone.

Before the plan (based on the model) can be carried out on the object, the model (and machining system) must be referenced with respect to the physical object, a process typically referred to as registration.

The registration process relies on correlation of identifiable landmarks, in both the object and in the model. Landmark positions can be identified in the model by means of image processing and on the object by means of digitization using a measurement device. At least three landmarks are needed to register the object with its model.

The registration can, however, be incorrect due to improper identification of landmarks on either or both the model and the object. This may result in an incorrect overlay of the coordinate systems of the object and the model leading to false manipulation of the object. For example in surgery, the cavity planned in the model of the bone will be carried out at in an incorrect position and/or orientation.

The identification of incorrect registration transformation might be difficult or even impossible due to lack of additional landmarks (beyond the landmarks used for the registration process itself) to be used for verification.

In WO 2009/092164 a surgical system utilizing tissue feedback is described to use estimates of tissue properties along a predetermined trajectory and make adjustments to an automated surgical task based on the difference between the actual and expected tissue properties as measured by the surgical tool. The type of controller utilized in this device is a linear type controller where for example a force sensor provides the input signal and the automated device (robot) can be controlled based on this signal. An illustrative example is given in the application of drilling a hole for pedicle screw placement. In this example it is desirable that the drill bit remain in the inner channel of the pedicle, thus if the drill bit contacts the outer wall (cortical bone) of this channel, the controller can adjust the trajectory to move away from this boundary.

In U.S. Pat. No. 6,718,196 a method of advancing a tool such as a probe into tissue such as the brain under the control of a single degree of freedom actuator attached to a stereotactic frame is described. Also described is a numerical control mechanism trained to identify both abnormal tissues and blood vessels based on tissue properties. Sensors may include modalities such as force, interstitial pressure, oxygenation, blood flow, etc. An initial portion of the tool trajectory is used to gather training data towards training of the control algorithm. The invention enables surgical probe advancement to be stopped at a tissue boundary such as a blood vessel.

In US 2011/0306985, a method of controlling machining feed rate based on the hardness of the material being worked is introduced. Spatial variation of the hardness of the material (bone) is determined from medical image data. Thus, the feed rate of the milling device can be altered according to the local hardness, which is derived from the image data. Force feedback can also be used to adjust the feed rate.

Further, in US 2007/0225787 a steerable electrode and a device used to insert it into the body is disclosed. The insertion system comprises a device, which actively controls the tools position (i.e. insertion depth) based on sensing of applied forces at the tool tip.

In US 2007/0181139 a system and a method is described to empirically determine contact between a probe and a tissue surface. This information is determined through the use of a robotic manipulator and a probe having a sensor attached to its distal end. The robot successively moves the probe to different positions and records the corresponding tissue property. Tool position and orientation relative to the surface is then determined based on the variation of the probe measurements.

Further, US 2011/0112397 discloses a technique for determining the location of a bony structure surrounded by soft tissue through the use of a three-dimensional position tracking device and a needle probe. In essence the device functions similar to a digitizing coordinate measurement machine in that a probe is inserted through the soft tissue and contacts the bone registering a peak in force and thereby triggering recording of the needles spatial position. By repeating this step from multiple orientations and positions, a 3D map of the bony surface can be created. Similar, in DE 102005029002 an invention is described related to the measurement of tissue forces and stiffness's with a probe that is simultaneously tracked in space. Thus, a three-dimensional map of mechanical properties can be created. Additionally, in DE 10 2008 013 429 A1 an invention is described correlating forces at the distal end of a surgical instrument with the 3D position within the body, whereby focus of the application is on forces directed lateral to the tool axis.

WO 2010/147972 relates to an invention to provide feedback to a surgeon when a surgical probe could be nearing the outer boundary of the pedicle and thus prevent a breach. Predictions of force thresholds are based on preoperative medical image data, where image intensity values are correlated with bone properties.

In US 2004/0010190 a system and method for aligning an ultrasound imaging probe relative to a predefined target inside a body is described. The system can track and follow moving targets by means of a robotic mechanism, which can automatically adjust the tools position in response to commands from a control system. Additionally, a force sensor may also be utilized to maintain contact of the probe with the body.

Summarizing, the prior to date describes controlling of machines or machining parameters based on available tool sensor information, but does not provide adequate means of estimating the pose of a tool in an inhomogeneous body.

The underlying objective of the present invention is to provide a simple system and a method that enables self-referencing of the manipulation tool relative to the coordinate system of the model and thus to the object being processed.

This problem is solved by a system having the features of claim 1.

Accordingly, the system comprises a sensor being designed to be coupled to a tool for machining a cavity into the object along an actual trajectory, which sensor is further designed to generate an sensor output signal upon machining of said object by means of said tool, which sensor output signal depends on a material property of said object along said actual trajectory (e.g. a material density), an analyzing means connected to the sensor and being designed to compare said sensor output signal, particularly upon machining said object (i.e. in real-time), with the at least one or a plurality of pre-determined candidate output signals in order to determine a correlation/similarity between said signals that is used for determining the spatial position of the tool within the object. Determining a correlation/similarity between the sensor output signal and the candidate output signal(s) may involve or may be performed by determining a scalar quantity that represents a measure for a similarity/dissimilarity or correlation between the measured sensor output signal and the candidate (theoretical or predicted) output signals. Such a scalar quantity may be denoted as dissimilarity measure or correlation index and may be employed as a weight when forming averages. Then, the spatial position of the tool within the object may be determined from at least the model trajectory whose associated (expected) output signal shows the best similarity/correlation with the measured sensor output signal according to the determined measure (i.e. shows a certain correlation index or (small) dissimilarity measure). Further, several or all model trajectories may be used to determine the (current) spatial position of the tool within the object by computing a weighted average according to the correlation/similarity between the output signal measured by the sensor and the candidate output signals, which are each associated to a model trajectory in a unique manner.

Each of the candidate output signals is generated beforehand using said material property along an associated model trajectory in a material property model of said object, which can be represented by a suitable (particularly 3D) representation (image) of the object.

Determining the spatial position of the tool within the object may involve the determination of all six degrees of freedom, or less, of the tool forming a rigid body.

According to an aspect of the invention, said spatial position (pose) of the tool within the object may be determined using at least the model trajectory whose associated candidate output signal has a correlation index corresponding to the highest correlation among the correlations between the sensor output signal and the candidate output signals. Since the tool machines a cavity along its (actual) trajectory and has a positive fit with the cavity, the model trajectory whose associated candidate output signal has the highest correlation with the sensor output signal directly yields the most likely position of the tool. For instance, the end point (target point) of said model trajectory can be taken as the spatial position of the (tip of the) tool in conjunction with the orientation of said model trajectory (with respect to the object).

According to an aspect of the invention, the analyzing means may be configured to perform a linear transformation of at least a section (or the whole course) of the candidate output signal $Y_i$ to match the latter with the output signal X of the sensor, particularly according to $Z_i = bY_iT + c$, where $Z_i$ is the transformed candidate output signal, b is a scaling factor and c is a shift vector, and T is an optional orthogonal rotation matrix and wherein the analyzing means is designed to optimize b, c and optionally T such that the dissimilarity measures (correlation index) $d_i$ being defined as $d_i = \Sigma_j (X_j - Z_{ij})^2$ are minimal. Here, the analyzing means is configured to take the candidate output signal $Y_i$ showing the smallest $d_i$ among the candidate output signals as the one that correlates best with the measured sensor output signal. The associated model trajectory can then be used for determining the spatial position of the tool (e.g. by considering the end point of said model trajectory and its orientation (T) as the full spatial position of the tool as described above).

For a statistically more robust method, all model trajectories can be taken into account when determining the (current) spatial position of the tool according to a further aspect of the invention, but are then weighted with individual weights which reflect the similarity/correlation between the sensor output signal and the candidate output signals that are uniquely associated to their respective model trajectory. For each model trajectory the corresponding weight particularly is a function of the difference (distance) between the sensor output signal and the candidate output signal that is associated to this model trajectory, wherein particularly the respective weight is a function of the squared difference between the sensor output signal and the respective candidate output signal.

Such weighted averages may be performed over certain points of the model trajectories corresponding to each other, particularly the end points p of the model trajectories and/or their orientations $o_i$, when the individual model trajectory is represented as $p_i = e_i + lo_i$, wherein $e_i$ is the entry position into the object on a surface of the object, $o_i$ is the orientation of the model trajectory and l its length, wherein the analyzing means may be configured to take the weighted average over the end points $p_i$ and over the corresponding orientations $o_i$ as the full spatial position of the tool within the object.

According to an aspect of the invention, the system is able to scale the temporal (spatial) component of the sensor output signal (i.e. the time or position axis) to correspond to the candidate output signal based on one or more of the following components: Initial contact of the machining tool with a surface of the object, a feed rate of the tool (according to encoder values of the automated machining apparatus/movement generating device retaining the tool), or position measurements, e.g. by way of an external observer (for instance a stereo vision system), which return the 3D pose of the tool in the reference coordinate frame by way of triangulation.

According to a further aspect of the invention—for real-time estimation of the pose—the analyzing means is designed to compare (correlate) the whole current course of the sensor output signal, i.e., from a beginning of the actual trajectory to a current position of the tool along the actual trajectory and/or from the time where machining of the object started up to the current elapsed time during machining of said object, with a corresponding section (interval) of the course of said pre-determined candidate output signals upon machining the object e.g. by determining said correlation index for each of the pre-determined candidate output signals, wherein said analyzing means is designed to estimate a current spatial position (pose) of the tool with respect to the object by identifying the model trajectory whose associated candidate output signal has a current correlation index corresponding to the best (current) correlation among the candidate output signals, or by performing the above weighting procedure repeatedly to perform an ongoing determination of the current spatial position of the tool upon machining of the object.

This allows for estimating the pose of the tool in real-time during machining of the object along the actual trajectory (trying to reproduce a planned trajectory planned beforehand).

According to yet a further aspect of the invention, the system comprises said tool for machining said object. Particularly, the tool is formed as a drill, wherein particularly the drill comprises a drill bit (at the tip of the tool) that is designed to drill (e.g. machine) a drill hole (cavity) into the object along the actual trajectory, when the drill bit is pressed against the object upon rotating the drill about a longitudinal axis of the drill, along which the drill extends.

Preferably, the system further comprises a drive for rotating the drill around said longitudinal axis of the drill. Particularly, said drive is coupled to the drill via a drill chuck.

Especially with the tool being formed as a (cylindrical) drill, the actual trajectory is essentially a linear trajectory corresponding to a cylindrical drill hole or cavity drilled into said object.

In this case, the model trajectories are also defined as (essentially) linear trajectories. Preferably, said model trajectories are distributed around a planned trajectory along which the object is to be machined yielding the actual trajectory, wherein particularly the model trajectories are arranged in groups. Preferably, model trajectories in a group share the same entry point into the object. Further, each group preferably comprises a trajectory having the orientation of the planned trajectory as well as trajectories having an orientation that differs by a small angle from the orientation of the planned trajectory, preferably in the range of 0.1° to 3.0°, more preferably 1.5°.

According to a further aspect of the invention, the system comprises a modeling means being designed to arrange (group) the model trajectories in particular and to use said material property along the respective model trajectory as the respective candidate output signal. In this respect, the employed model of the object is represented by a tomographic 3D-image of the material property of the object consisting of a plurality of voxels (volume pixels) each indicating a certain value of the material property (e.g. bone density) of the object, wherein said 3D-image is particularly a CT-scan. Preferably, the modeling means is designed to discretize the respective model trajectory by dividing it into steps (bins) having a pre-defined step size, wherein for each step along the associated model trajectory voxels within a radius corresponding to a radius of the tool in a lateral plane normal to the respective model trajectory are integrated yielding a material property value, i.e. a value of the respective candidate output signal, associated with the respective step (position) along the respective model trajectory.

Preferably, the modeling means is further designed to represent the candidate output signals as vectors, wherein particularly the dimension of the respective vector corresponds to the length of the respective model trajectory in units of a certain step size. Likewise, also the analyzing means is preferably designed to represent the sensor output signal and the candidate output signals as vectors $X$, $Y_i$, $i$ labeling the candidate output vectors, wherein particularly the dimensions of these vectors correspond to a current length of the respective (model) trajectory in units of a certain step size.

The analyzing means and/or modeling means may be formed by a computer and a corresponding software (that may be loaded into the RAM of the computer) being executed by the computer. In this case the sensor is preferably connected to the computer via an interface. However, the analyzing means and/or the modeling means may also be formed as a stand-alone device.

According to a preferred embodiment of the invention, the sensor is a 6 degree of freedom semi-conductor strain gauge based force sensor that is designed to sense a force exerted by the object onto the tool upon machining said object, particularly a force exerted by the object that is to be machined onto the drill bit along the longitudinal axis of the drill. Furthermore, forces applied at the tip of the drill bit can be transformed into a suitable coordinate system (coordinate system of the force sensor) such that forces and torques can be correctly distinguished.

Alternatively, or in addition, also other quantities like a torque acting on the drill (e.g. oriented along the tool's/drill's longitudinal axis) may be sensed by corresponding sensors and compared to corresponding material properties of the object so that one has on the one hand an output signal that can be measured by the respective sensor corresponding (or correlating) to a material property (or some other characteristics of the object) and on the other hand said material property (characteristics) that can be used as an candidate output signal. Such a pairing of actually measured properties is given, when the measured quantity significantly correlates with the theoretically constructed (candidate) output signal, i.e., the material property (physical quantity) itself. Other material properties that may be considered are electrical or magnetic impedance of the object, rigidity of the object or the like.

In case of (drilling) forces measured by said sensor one finds that these forces correlate well with the (bone) density of the object (e.g. mastoid) at the tool tip, which allows for estimation of the location of the tool (drill) within the object with an accuracy of around the diameter of the cavity/drill. Such an accuracy level is sufficient to ensure that deviations from the planned trajectory are observed, and the integrity of critical structures within the facial recess (in case of the mastoid bone) is ensured.

According to a further aspect of the invention, the system not only enables an estimation of the position of the tool within (or with respect to) the machined object, but also to move the tool by means of a movement generating means of the system that may be coupled to the analyzing means, which movement generating means is designed to automatically move the tool along a planned trajectory (resulting in machining the object along the actual trajectory). The movement generating means may be or may form part of an automated tool guidance system including but not limited to robot systems, computer numerically controlled machining systems etc. Particularly, the movement generating means is formed as a robot arm. Further, the sensor is preferably arranged between the drill chuck and the movement generating means, wherein particularly the drill chuck is coupled to the movement generating means via a coupling means comprising an interface via which the coupling means can be (releasably) coupled to the movement generating means (e.g. robot arm). Preferably, said sensor is provided on the coupling means.

According to yet another preferred aspect of the invention, the system is designed to generate a warning signal that can be perceived by a user operating the system and/or a stop signal that causes to the drive and/or the actuators (movement generating means) of the system to stop, when a distance between the current position of the tool (actual trajectory) and a planned trajectory exceeds a pre-defined threshold value.

Preferably the system further comprises a controlling means interacting with said movement generating means and eventually also with the drive in order to control these devices. Of course the controlling means can be formed as a stand-alone device or a part thereof, but may also be formed by corresponding software executed on said computer or even on a separate computer. The drive/movement generating means is then connected to such a computer via an interface.

According to one implementation of the system, the controlling means is designed to control the movement generating means upon machining of the object such that the current position of the tool (actual trajectory) asymptotically approaches a current planned position of the tool (planned trajectory). Further, the controlling means may be designed to control the movement generating means and drive upon machining of the object such that a current velocity of the tool along the actual trajectory approaches a current planned (reference) velocity of the tool.

The problem underlying the present invention is further solved by a method having the features of claim 10.

According thereto, the method according to the invention comprises the steps of: providing at least one, particularly a plurality of candidate output signals, corresponding to a material property of the object along associated model trajectories in a material property model of said object (e.g. in a vicinity of a planned trajectory), providing a sensor output signal depending on a material property along an actual trajectory in said object, automatically determining a correlation/similarity between said sensor output signal and the at least one candidate output signal or the plurality of candidate (model) output signals in order to determine the spatial position of the tool within the object (see also above).

The object may be any (artificial or natural) material that can be machined, particularly drilled. In an aspect of the invention, the object may be formed by living cells or tissues of the (human or animal) body, particularly a bone (alive or dead).

According to another aspect of the invention, the object may be any (machinable) object that is not formed by living cells or tissues of the living human or animal body.

Further, according to an aspect of the invention, the actual machining of the object by means of the tool needs not to be a part of the method according to the invention, i.e., the tool may machine the object along the actual trajectory beforehand. The sensor output signal generated thereby is then used in order to determine the spatial position of the tool within the object, which tool machined the object along the actual trajectory beforehand.

According to an aspect of the method according to the invention, the candidate output signal that correlates best/shows the highest similarity with the measured sensor output signal is determined and used for estimating the spatial position of the tool within the object, which may be determined as an end point of the model trajectory associated to said best-correlated candidate output signal and/or as an (corresponding) orientation of said model trajectory.

Further, for determining a measure for said correlation/similarity a linear transformation of at least a section of each candidate output signal $Y_i$ may be computed according to an aspect of the invention to match the latter with the sensor output signal X of the sensor, particularly according to $Z_i=bY_iT+c$, where $Z_i$ is the transformed candidate output signal, b is a scaling factor and c is a shift vector, and T is an optional orthogonal rotation matrix, and wherein b, c and optionally T are chosen such that the dissimilarity measure $d_i$ being defined as $d_i=\Sigma_j(X_j-Z_{ij})^2$ (summation over j) becomes a minimum, wherein particularly the candidate output signal $Y_i$ that correlates best with the sensor output signal X is taken as the candidate output signal ($Y_i$) being associated to the smallest $d_i$ among all candidate output signals.

According to yet a further aspect, the correlation/similarity may be expressed in form of weights $w_i$ for each model trajectory, wherein particularly each weight $w_i$ is a function of the difference between the sensor output signal and the respective candidate output signal, particularly the squared difference. Then, for determining the spatial position of the tool within the object, a weighted average over corresponding points, particularly end points $p_i$, of the model trajectories and/or over orientations $o_i$ of the model trajectories may be automatically performed, wherein each of said points $p_i$ and/or orientations $o_i$ is weighted using its associated weight $w_i$.

Preferably, particularly for determining the current spatial position of the tool within the object in real-time, a correlation between the whole current course of the sensor output signal and a corresponding section of the at least one pre-determined candidate output signal or each of the pre-determined candidate output signals is automatically determined, particularly upon machining the object with said tool.

Preferably, the sensor output signal is generated as a function of the position of the tool along the actual trajectory and/or as a function of the time elapsed during machining of the object with the tool along the actual trajectory, wherein for simplifying the comparison between the sensor output signal and the (predicted) candidate output signals, the sensor output signal and/or the at least one candidate output signal or plurality of candidate output signals is preferably scaled along a time or position axis, particularly so as to match the extension of the sensor output signal along the time or position axis with the corresponding extension of the at least one candidate output signal or with the corresponding extensions of the plurality of candidate output signals. Particularly in case said signals are represented as vectors, these vectors have the same dimension which simplifies the calculation of the above-described weights and transformations.

Preferably said tool is a drill, so that the model trajectories are (essentially) linear trajectories, wherein particularly said model trajectories are (automatically) distributed around a planned trajectory along which the object is to be machined (yielding the actual trajectory), wherein particularly the model trajectories are distributed in groups around the planned trajectory, wherein the model trajectories in each group have the same entry point into the object. Preferably, each group comprises a trajectory having the orientation of the planned trajectory as well as trajectories having an orientation that differs from the orientation of the planned trajectory by a small angle, preferably in the range of 0.1° to 3.0°, more preferably 1.5°.

According to an aspect of the method according to the invention, said material property along the respective model trajectory is preferably used as the respective candidate output signal. Preferably, said sensor output signal is a force, wherein the material property preferably is a density, particularly a bone density (see above), correlating therewith.

In particular, the model from which the candidate output signals are (automatically) generated is represented by a tomographic 3D-image of the material property of the object consisting of a plurality of voxels each indicating a certain value of the material property (e.g. bone density). Particularly, said image is created by a (cone beam) CT-scan of the object in beforehand.

The candidate output signals are preferably discretized along the respective model trajectory by dividing them into steps having a pre-defined step size, wherein for each step along the associated model trajectory voxels within a radius corresponding to a radius of the tool in a lateral plane normal to the respective model trajectory are (automatically) integrated yielding a material property value, i.e. a value of the respective candidate output signal associated to the respective step (position) along the respective model trajectory.

Preferably, the sensor output signal corresponds to a force exerted by the object onto the tool upon machining said object by means of said tool, wherein particularly the tool is formed as a drill as described above.

Accordingly, the material property is preferably a density of the object, particularly a bone density. Then, the sensor output signal may be in general represented as a force vector and the candidate output signals as (axial) density vectors.

Furthermore, according to an aspect of the invention, a warning signal is generated upon moving the tool within the objet along the actual trajectory, when a distance between a current spatial position of the tool that is determined by way of correlation as described above and a planned (theoretical) trajectory in the object exceeds a pre-defined threshold value. Then, according to a further aspect of the invention, the tool may also be automatically stopped.

According to a further variant of the method according to the invention, machining of the object by means of the tool may be automatically guided by a movement generating means, wherein moving the tool (machining the object) along the actual trajectory is controlled such that the current spatial position of the tool within the object determined by way of correlation approaches a current planned spatial position of the tool along a planned trajectory. Further, said movement generating means for moving the tool along the actual trajectory upon machining the object and a drive for rotating the tool (drill) around its longitudinal axis is preferably controlled such upon machining of the object that a current velocity of the tool approaches a current planned velocity of the tool.

Finally, the problem according to the invention is also solved by a computer program product (software) having the features of claim 15, which is particularly stored on a computer readable medium or downloadable (e.g. from computer), and which is particularly designed to be loaded into the memory of a computer (or the present system), wherein the computer program product is designed to conduct—upon being executed on a computer (or the present system)—the following steps: generating at least one candidate output signal based on a material property of an object along a model trajectory in a model of said object, the model trajectory being associated with at the least one candidate output signal, reading a sensor output signal depending on the material property along an actual trajectory in said object as an input to the computer program, and determining a correlation between the sensor output signal and the at least one candidate output signal for determining the spatial position of the tool within the object, Further, the computer program product according to the invention may be particularly designed to conduct, when being executed on a computer (or on the present system), also at least one of the steps stated in one of the claims 10 to 14 (as well as at the end of the present specification relating to claims 10 to 14)

Further features and advantages of the invention shall be described by means of a detailed description of embodiments with reference to the Figures, wherein FIG. 1 shows a schematic view of a tool machining an object (mastoid) along a planned trajectory resulting in a cavity along an actual trajectory, wherein during machining an sensor output signal is generated by means of sensor coupled to the tool, which corresponds to the force measured at the tip of the tool (drill bit);

FIG. 2 shows a schematic view showing the generation of candidate (model) output signals by considering a material property (density) along model trajectories, which material property (density) correlates with said force according to FIG. 1, as well as correlating said candidate output signals with the sensor output signal according to FIG. 1 for estimating the most likely position of the tool within the object;

Figure 5:
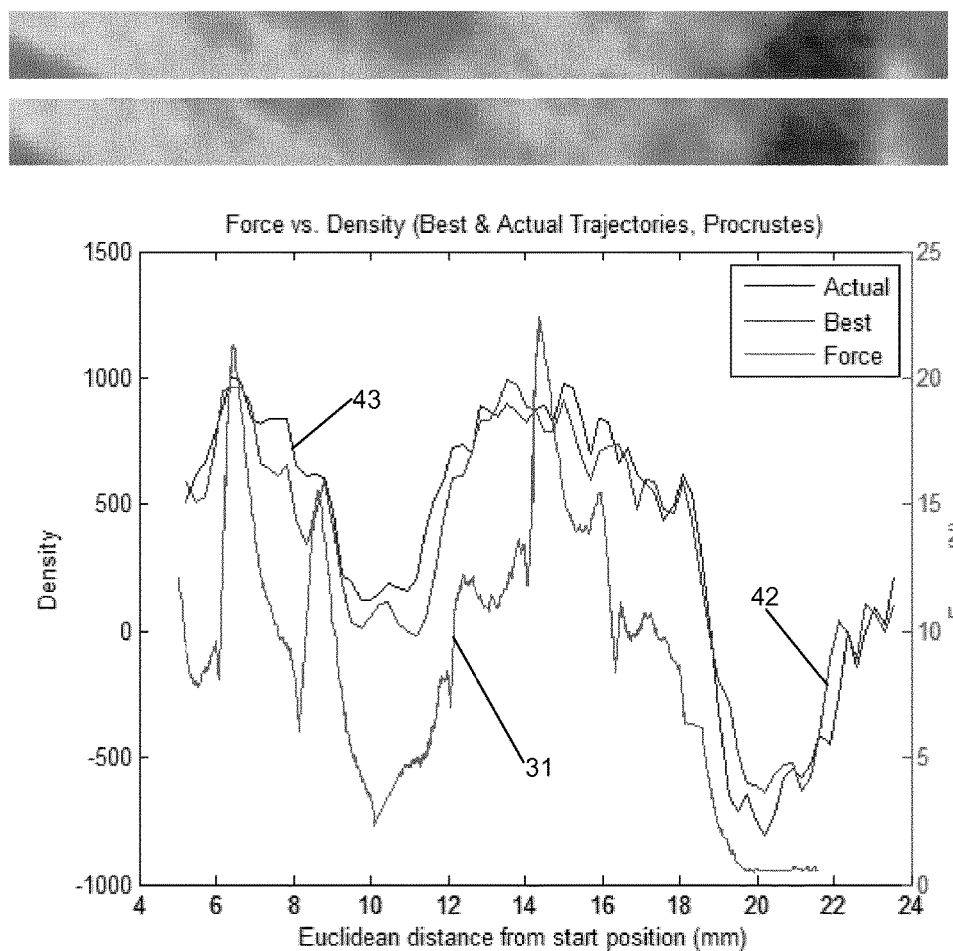
Figure 6:
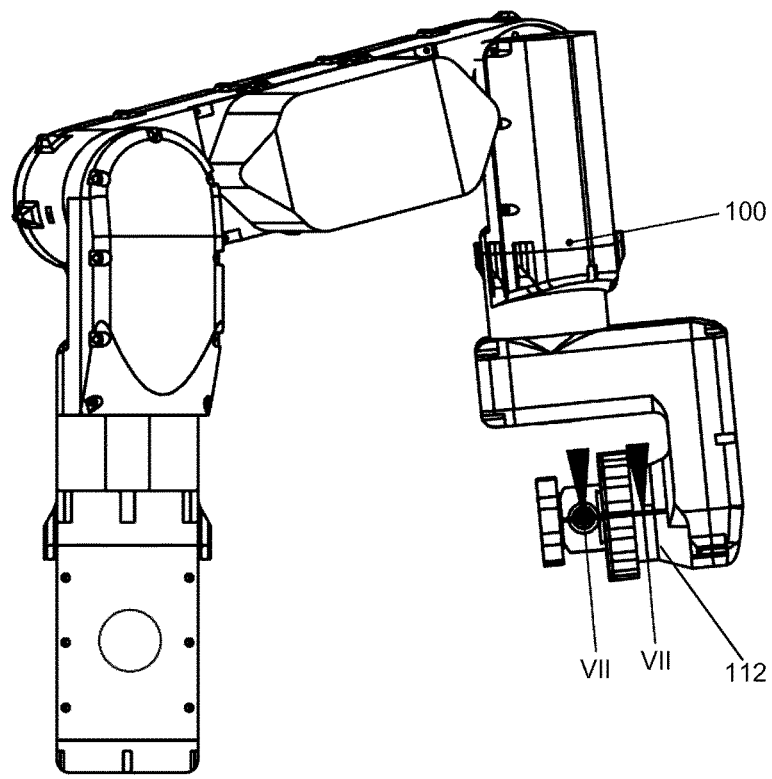
Figure 7:
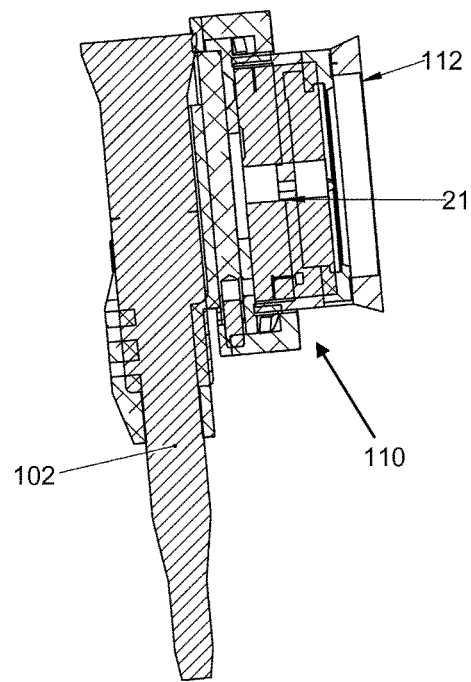

FIG. 5 shows a comparison of the density (candidate output signal) and force (measured sensor output signal) between the actual (drilled) trajectory and the best correlated candidate output signal (density vector); on top, the upper slice represents the area that was actually drilled while the lower slice shows the best correlated density (candidate output signal) along the associated model trajectory;

FIG. 6 shows a movement generating means for moving the tool (drill) in the form of a robot arm; and FIG. 7 shows a detail of FIG. 6.

Figure 1:
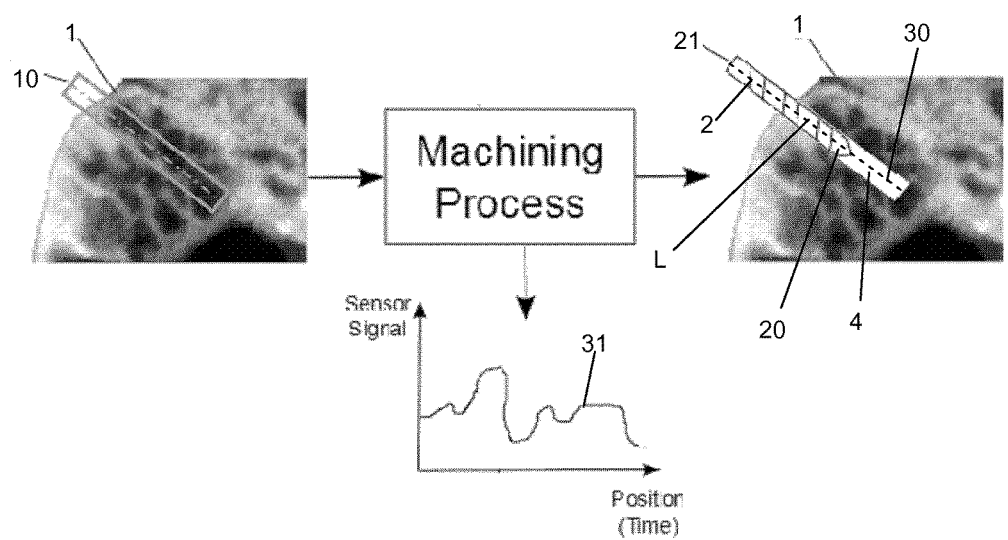

FIG. 1 shows a model of an object 1 (CT-Image) stating the density (material property) of the object in space, which object 1 is to be machined (drilled) by means of a tool 2 that is formed as a drill. While drilling along a planned trajectory 10 into the object 1 resulting in a cavity 4 extending along a (linear) actual trajectory 30, the force at the tip (drill bit) 20 of the tool 2 that reflects the varying density along the actual trajectory 30 is measured by means of a sensor 21 coupled to the tool resulting in an sensor output signal 31 over the position along the actual trajectory 30 and/or time of the drilling process. The sensor output signal 31 is preferably represented as a vector where the position/time axis of the sensor output signal 31 is discretized into bins (intervals) and the components of the vector correspond to the values of the sensor output signal 31 for the respective position/time bin (step).

Figure 2:
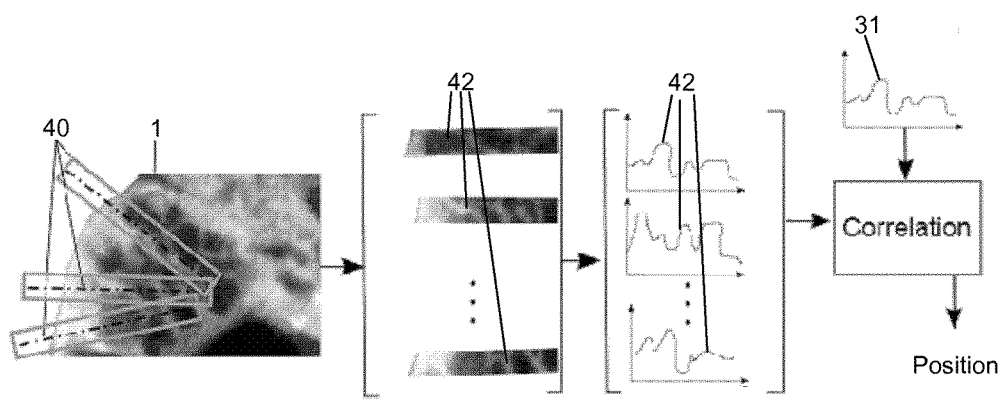

Before drilling into the object 1 by means of the tool 2, a plurality of candidate output signals 41 are generated according to FIG. 2 by considering a corresponding plurality of model trajectories 40 and taking the density 42 along the respective model trajectory as the respective "candidate" output signal 42, wherein the density may be integrated (averaged) in lateral planes across the respective model trajectory 40 over an area corresponding to the associated cross section of tool 2.

Also here the candidate output signals 42 are discretized according to the bin (step) size of the measured sensor output signal 31 and represented as vectors. This allows one to easily correlate the sensor output signal 31 with candidate output signals 42 (entry by entry).

In detail, the original output (sensor) signal 31 during object manipulation is correlated with corresponding portions of all available instances of the candidate (anticipated) output signals 42. The system then selects the candidate output signal 42 that correlates best with the measured sensor output signal 31. The corresponding model trajectory 40 then allows for estimating the most likely position of tool 2, since this position then corresponds to said (current) model trajectory 40 within the object 1 being manipulated. Alternatively, averages may be computed as described below.

Figure 3:
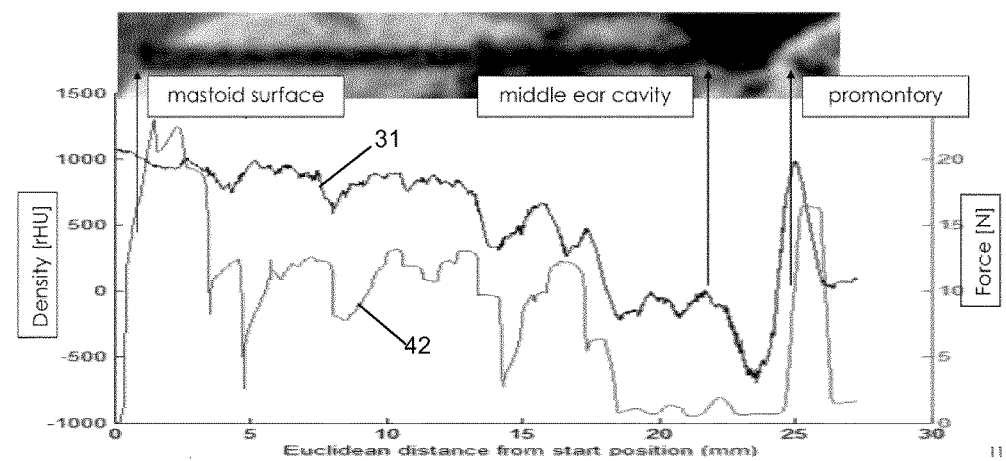
FIG. 3 shows a comparison between the force measured upon drilling into the mastoid as well as a corresponding candidate output signal (density of the mastoid; model information)

FIG. 3 shows a comparison of the tool sensor data (sensor output signal 31 representing the drilling force) with the corresponding model information (here: density (candidate output signal) 42 of the object material from computed tomography along a corresponding model trajectory 40) as well as an estimation of the tool 2 within the object 1 itself.

Figure 4:
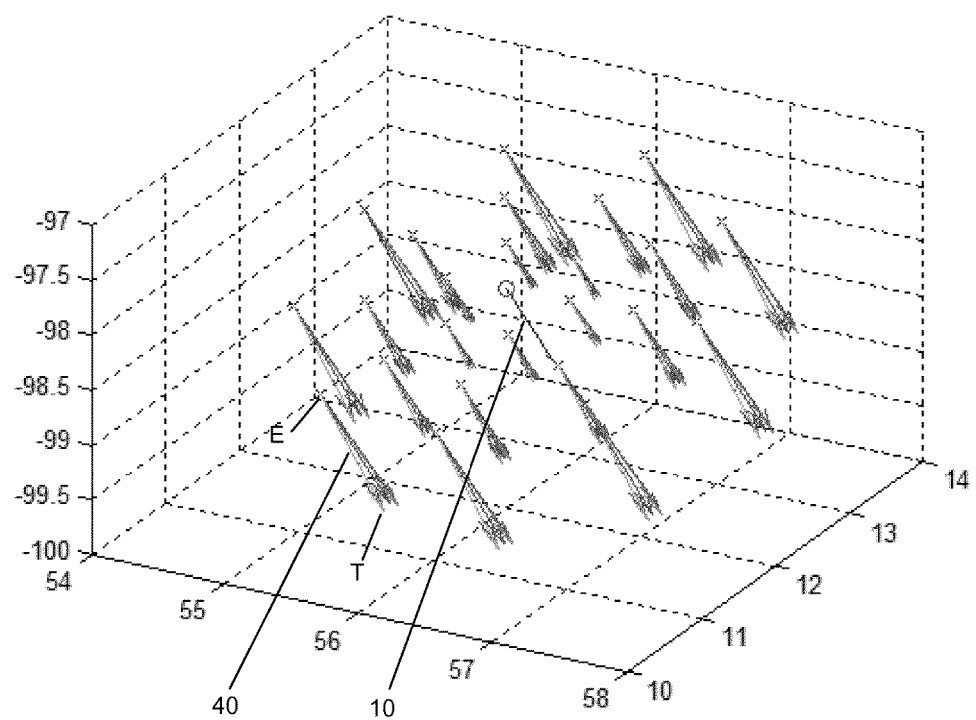
FIG. 4 shows an example of the distribution of model trajectories around a planned trajectory (actual trajectory)

FIGS. 4 and 5 illustrate a quantitative test of the present system and method. Here, a pre-op cone-beam CT scan was taken wherein 4 trajectories planned through the mastoid bone of a human are analyzed below. Each of these trajectories was drilled using a robotic system (movement generating means) while recording force data by means of a sensor as discussed above. The drilling feed-rate was 0.3 mm/s, the drill speed was 5000 RPM.

After drilling, a wire was inserted into each of the (actual) trajectories to aid segmentation (discretization into bins) and a post-operative DVT was taken. The pre- and post-op images were then co-registered and the actual drilled trajectory calculated.

A square region of interest (3×3 mm) was defined around the planned trajectory $P_o$. Five candidate trajectories were calculated at each spaced entry position ($e_i$) spaced at 0.3 mm with orientation $o_i$ and length $l$ according to equation 1.

$$p_i = e_i + l * o_i \quad (1)$$

Density values (corresponding to the candidate output signal) were calculated along each $p_i$ for a total of 605 candidate trajectories as seen in FIG. 4.

For each model trajectory 40, its corresponding axial density vector $D_i$ was calculated by integrating all voxels in a given lateral plane (defined as normal to the drilling vector $p_i$ and within the radius of the drill 2 used. The step size in axial direction was defined by the length of the model trajectory 40 divided by the desired number of points. In this case, n'=100. The resulting vector is finally normalized about its mean ($\hat{D}_i$).

The force vector (F) obtained during drilling was pre-processed to remove artifacts from the drilling procedure (zero force during feed reversal (pecking)) and subsampling (scaling) in the time domain was performed to match the force vector length (dimension) with that of the density vector (n'=100). The resulting force vector was normalized ($\hat{F}$) about its mean, and a squared difference was computed between the normalized force and each (i) of the candidate density vectors as in equation (2).

$$r_i = (\hat{F} - \hat{D}_i)^2 \quad (2)$$

The mean of this vector ($\bar{r}_i$) is then normalized over all trials ($\hat{r}_i$) and the weights defined as:

$$w_i = (1 - \hat{r}_i)^q \quad (3)$$

Where q determines the relative weighting of each result. A value of q=10 was determined to be appropriate and is discussed further in the section following.

The position of the drill was then estimated by calculating the weighted mean position (4) from the target position $p_i$ of each of the defined trajectories, n as the total number of alternative trajectories and $w_i$ as the weight representing the individual force-density correlation:

$$\bar{p} = \frac{\sum_{i=1}^{n} w_i * p_i}{\sum_{i=1}^{n} w_i} \quad (4)$$

A confidence value was also defined (5). This represents a comparison between the current result and the best possible result, defined as the case with a single well matched outcome and no other matching trajectories.

$$c = \frac{\sum_{i=1}^{n} w_i^2}{\sum_{i=1}^{n} w_i} * d \quad (5)$$

Where c is the confidence and d is a further weighting factor (6), which is a function of the spread of the trajectories. Here s is a distance weighting exponent, $l_{max}$ is the maximum distance of any trajectory from the planned trajectory and all other variables are as previously defined.

$$d = \left( \left( l_{max} - \sqrt{\frac{\sum_{i=1}^{n} w_i * (p_i - \bar{p})}{\sum_{i=1}^{n} w_i}} \right) * \frac{1}{l_{max}} \right)^s \quad (6)$$

In order to calculate the tool direction, the orientation of each of the trajectories undergoes the same process as described above; the direction which is closest to the true tool orientation should be correlated most closely and the weighted mean vector direction should reflect this.

The results of the present offline analysis, as described above are shown in Table.

TABLE 2

Error in calculated positions and confidence of estimates.

| Trial | Entry error (mm) | Target error (mm) | Angular Error (°) | Confidence (%) |
|---|---|---|---|---|
| 1 | 0.22 | 0.25 | 0.06 | 9.02 |
| 2 | 0.20 | 0.28 | 0.18 | 5.77 |
| 3 | 0.41 | 0.27 | 0.32 | 3.59 |
| 4 | 0.17 | 0.35 | 0.43 | 9.53 |
| Mean | 0.25 | 0.29 | 0.25 | 6.98 |
| Std | 0.11 | 0.05 | 0.16 | 2.81 |

An example of the actual density 43 along the drilled path 30, the best correlated density vector 42, and force 31 along the drilled actual trajectory 30 are shown in FIG. 5. Also shown (top part of FIG. 5) is a slice of the object 1 (model) displaying the actual density in the drilled cavity (upper part) as well as the density that correlated best with the measured force (sensor output signal).

Further, FIG. 6 shows in conjunction with FIG. 7 a movement generating means 100 of the system according to the invention by means of which the tool (drill) 2 can be automatically moved (e.g. controlled by the afore-described controlling means). For this, the movement generating means 100 may be controlled by a controlling means. According to FIGS. 6 and 7 the movement generating means 100 preferably uses a serial kinematics, i.e., is formed as a robot arm, that comprises preferably at least six axes (preferably rotational axes, but a linear axis may also be present) being represented by corresponding (rotating or, if present, translational) joints, respectively. Each axis (joint) may be actuated by a corresponding actuator. Thus, the drill 2 attached to the robot arm 100 via a drill chuck 102 can approach any target point in a workspace of the robot arm 100 with an arbitrary orientation.

For coupling the drill chuck 102 to the robot arm 100, a coupling means 110 is provided to which the drill chuck 102 is connected and which provides an interface 112 via which the coupling means is coupled to the free end of the robot arm 100.

The sensor 120 for sensing the forces acting on the drill upon machining an object is preferably arranged in the coupling means 110. i.e., between the drill chuck 102 and the robot arm 100.

A drive for driving a drill fastened to the (thinner) free end of the drill chuck 102 can be connected to the other (broader) free end of the drill chuck 102 shown in FIG. 7.

In the following further variants of the present invention that may also be formulated as sub claims referring back to at least one of the claims appended at the end of the specification.

Regarding the system according to the invention, the analyzing means is preferably designed to determine a correlation between the whole current course of the sensor output signal (31) and a corresponding section of the at least one pre-determined candidate output signal (42) or corresponding sections of each of the pre-determined candidate output signals (42) upon machining the object (2) for determining the current spatial position of the tool within the object (1).

In a further variant, the system is designed to generate said sensor output signal (31) by means of said sensor (21) as a function of the position of the tool (2) along the actual trajectory (30) and/or as a function of the time elapsed during machining of the object (1).

In a further variant, the system is designed to scale the sensor output signal (31) along a time or position axis, particularly so as to match the extension of the sensor output signal (31) along the time or position axis with the corresponding extension of the at least one candidate output signal (42) or with the corresponding extensions of the plurality of candidate output signals (42).

In a further variant, the actual trajectory (30) is a linear trajectory.

In a further variant, the at least one model trajectory (40) or the model trajectories (40) are linear trajectories, wherein particularly said model trajectories (40) are distributed around a planned trajectory (10) along which the object (1) is to be machined yielding the actual trajectory (30), wherein particularly the model trajectories (40) form groups, wherein model trajectories in a group have the same entry point (E) into the object (1), and wherein each group comprises a model trajectory (40) having the orientation of the planned trajectory (10) as well as model trajectories (40) having an orientation that is different from the orientation of the planned trajectory (10).

In a further variant, the system comprises a modeling means being designed to generate the at least one candidate output signal or the plurality of candidate output signals (42) as said material property along the respective model trajectory (40), wherein particularly the model of the object (1) is represented by a 3D-image of the material property of the object (1) consisting of a plurality of voxels each indicating a certain value of the material property, and wherein particularly the modeling means is designed to integrate voxels within a radius corresponding to a radius of the tool (2) in a lateral plane normal to the respective model trajectory (40).

In a further variant, the sensor output signal corresponds to a force exerted by the object (1) onto the tool (2) upon machining said object (1), particularly a force exerted by the object (2) onto the drill bit (21) along the longitudinal axis (L) of the drill (2).

In a further variant, the drive is coupled to the drill (2) via a drill chuck (102).

In a further variant, the system comprises a movement generating means (100) for moving the tool (2) along the actual trajectory (30) for machining the object (1), wherein particularly the movement generating means (100) is formed as a robot arm (100).

In a further variant, the drill chuck (102) is coupled to the movement generating means (100), particularly via a coupling means (110) comprising an interface (112) that is designed to be coupled to said robot arm (100).

In a further variant, the sensor (21) is arranged between the movement generating means (100) and the drill chuck (102), wherein particularly the sensor (21) is arranged in said coupling means (110).

In a further variant, the system is designed to generate a warning signal when a distance between a spatial position of the tool (2) within the object (1) and a planned trajectory (10) exceeds a pre-defined threshold value.

In a further variant, the system is designed to stop the drive and/or the movement generating means (100) when a distance between a spatial position of the tool (2) and a planned trajectory (10) exceeds a pre-defined threshold value.

In a further variant the system comprises a controlling means for controlling the tool (2), wherein particularly the controlling means is designed to control the movement generating means (100) upon machining of the object (1) such that a determined current spatial position of the tool (2) within the object (1) approaches a current planned spatial position of the tool (2) along a planned trajectory (10), and wherein particularly the controlling means is designed to control the movement generating means (100) and drive upon machining of the object (1) such that a current velocity of the tool (2) approaches a current planned velocity of the tool (2).

Regarding the method according to the invention, for determining the current spatial position of the tool (2) within the object (1) a correlation between the whole current course of the sensor output signal (31) and a corresponding section of the at least one pre-determined candidate output signal (42) or corresponding sections of each of the pre-determined candidate output signals (42) is preferably determined, particularly upon machining the object (2) with said tool (2).

In a further variant of the method, the sensor output signal (31) is generated as a function of the position of the tool (2) along the actual trajectory (30) and/or as a function of the time elapsed during machining of the object (1) with the tool (2) along the actual trajectory (30).

In a further variant of the method, the sensor output signal (31) is scaled along a time or position axis, particularly so as to match the extension of the sensor output signal (31) along the time or position axis with the corresponding extension of the at least one candidate output signal (42) or with the corresponding extensions of the plurality of candidate output signals (42).

In a further variant of the method, the at least one model trajectory or the model trajectories (40) are linear trajectories, wherein particularly said model trajectories (40) are distributed around a planned trajectory (10) along which the object (1) is to be machined yielding the actual trajectory (30), wherein particularly the model trajectories (40) are arranged to form groups, wherein model trajectories (40) in a group have the same entry point (E) into the object (1), and wherein each group comprises a model trajectory (40) having the orientation of the planned trajectory (10) as well as model trajectories (40) having an orientation that is different from the orientation of the planned trajectory (10).

In a further variant of the method, the at least one candidate output signal (42) or a plurality of candidate output signals (42) are generated as a function of said material property along the respective model trajectory (40), wherein particularly the model of the object (1) is represented by a 3D-image of the material property of the object consisting of a plurality of voxels each indicating a certain value of the material property, and wherein particularly voxels within a radius corresponding to a radius of the tool in a lateral plane normal to the respective model trajectory (40) are integrated in order to generate the respective candidate output signal (42).

In a further variant of the method, the sensor output signal (31) corresponds to a force exerted by the object (1) onto the tool (2) upon machining said object (1), wherein particularly the tool (2) is formed as a drill, wherein particularly the drill comprises a drilling bit (20) that is designed to drill a hole (4) into the object (1), when the drilling bit (20) is pressed against the object (1) upon rotating the drill (2) about a longitudinal axis (L) of the drill (2), along which the drill (2) extends, wherein the sensor output signal corresponds to a force exerted by the object (2) onto said drill bit (21) along the longitudinal axis (L) of the drill.

In a further variant of the method, the material property is a density of the object (1), particularly a bone density.

In a further variant of the method, a warning signal is generated when a distance between a determined current spatial position of the tool (2) within the object (1) and a planned trajectory (10) exceeds a pre-defined threshold value.

In a further variant of the method, a movement of the tool (2) along the actual trajectory is stopped when a distance between a determined current spatial position of the tool (2) within the object (1) and a planned trajectory (10) exceeds a pre-defined threshold value.

In a further variant of the method, a movement of the tool (2) along the actual trajectory is controlled such that the determined current spatial position of the tool (2) within the object (1) approaches a current planned spatial position of the tool (2) along a planned trajectory (10), and wherein particularly a movement generating means (100), particularly a robot arm, for moving the tool (2) along the actual trajectory (30) upon machining the object (1) and a drive for rotating the tool (2) around its longitudinal axis (L) is controlled upon machining of the object (1) such that a current velocity of the tool (2) approaches a current planned velocity of the tool (2).

The invention claimed is:

1. A system for estimating the spatial position of a tool within an object, particularly in the form of a human bone that is to be machined with said tool, comprising:
    a sensor being designed to be coupled to said tool, which sensor is further designed to generate a sensor output signal upon machining of said object along an actual trajectory, which sensor output signal depends on a material property of said object along said actual trajectory,
    an analyzing means being designed to determine a spatial position of the tool within the object, wherein for determining said spatial position the analyzing means is designed to determine a correlation between said sensor output signal, particularly upon machining said object, and at least one pre-determined candidate output signal being generated in beforehand using said material property along an associated model trajectory in a model of said object.

2. The system according to claim 1, characterized in that, for estimating said spatial position the analyzing means is designed to determine a correlation between said sensor output signal, particularly upon machining said object, and a plurality of pre-determined candidate output signals, each candidate output signal being generated in beforehand using said material property along an associated model trajectory in a model of said object.

3. The system according to claim 2, characterized in that for determining the spatial position of the tool within the object, the analyzing means is designed to determine at least the candidate output signal that correlates best with the sensor output signal, wherein particularly the analyzing means is designed to determine the spatial position of the tool within the object as an end point of the model trajectory associated to said best-correlated candidate output signal and/or an orientation of said model trajectory.

4. The system according to claim 3, characterized in that for determining at least the candidate output signal ($Y_i$) that correlates best with the sensor output signal (X) the analyzing means is designed to perform a linear transformation of at least a section of each candidate output signal ($Y_i$) to match the latter with the sensor output signal (X) of the sensor, particularly according to $Z_{,i}=bY_iT+c$, where $Z_i$ is the transformed candidate output signal, b is a scaling factor and c is a shift vector, and T is an optional orthogonal rotation matrix, and wherein the analyzing means is designed to choose b, c and optionally T such that the dissimilarity measure $d_i$ being defined as $d_i=\Sigma_j(X_j-Z_{,ij})^2$ becomes a minimum, wherein particularly the analyzing means is designed to determine the candidate output signal ($Y_i$) that correlates best with the sensor output signal (X) as the candidate output signal ($Y_i$) being associated to the smallest $d_i$.

5. The system according to claim 2, characterized in that the analyzing means is designed to compute a weight ($w_i$) associated to each model trajectory as a measure for the correlation between the sensor output signal and the respective candidate output signal associated to the respective model trajectory, wherein particularly each weight ($w_i$) is a function of the difference between the sensor output signal and the respective candidate output signal, particularly the squared difference, wherein particularly for determining the spatial position of the tool within the object, the analyzing means is designed to compute a weighted average over corresponding points, particularly end points ($p_i$), of the model trajectories and/or over orientations ($o_i$) of the model trajectories, wherein each of said points ($p_i$) and/or orientations is weighted with the weight ($w_i$) associated to the model trajectory to which the respective point ($p_i$) and/or orientation ($o_i$) belongs.

6. The system according to claim 1, characterized in that the system further comprises a tool for machining said object.

7. The system according to claim 1, characterized in that the tool is formed as a drill, wherein particularly the drill comprises a drilling bit that is designed to drill a drill hole into the object, when the drilling bit is pressed against the object upon rotating the drill about a longitudinal axis (L) of the drill, along which the drill extends.

8. The system according to claim 7, characterized in that the system comprises a drive for rotating the drill around said longitudinal axis (L) of the drill.

9. The system according to claim 1, characterized in that the material property is the density of the object, particularly a bone density.

10. A method for estimating the spatial position of a tool within an object, the method comprising the steps of:
generating at least one candidate output signal based on a material property of the object along a model trajectory in a model of said object, the model trajectory being associated with the at least one candidate output signal,
providing a sensor output signal depending on the material property along an actual trajectory in said object,
determining a correlation between the sensor output signal and the at least one candidate output signal for determining the spatial position of the tool within the object.

11. The method according to claim 10, characterized in that for estimation of said spatial position, a correlation between said sensor output signal, particularly upon machining said object, and a plurality of pre-determined candidate output signals is determined, each candidate output signal being generated beforehand using said material property along an associated model trajectory in a model of said object.

12. The methods according to claim 11, characterized in that the spatial position of the tool within the object is defined as the candidate output signal that correlates best with the sensor output signal, wherein particularly the spatial position of the tool within the object is determined as an end point of the model trajectory associated to said best-correlated candidate output signal and/or as an orientation of said model trajectory.

13. The method according to claim 12, characterized in that for determination of the candidate output signal ($Y_i$) that correlates best with the sensor output signal (X) a linear transformation of at least a section of each candidate output signal ($Y_i$) is performed to match the latter with the sensor output signal (X) of the sensor, particularly according to $Z_i=bY_iT+c$, where $Z_i$ is the transformed candidate output signal, b is a scaling factor and c is a shift vector, and T is an optional orthogonal rotation matrix, and wherein b, c and optionally T are chosen such that the dissimilarity measure $d_i$ being defined as $d_i=\Sigma_j(X_j-Z_{ij})^2$ becomes a minimum, wherein particularly the candidate output signal ($Y_i$) that correlates best with the sensor output signal (X) is determined as the candidate output signal ($Y_i$) being associated to the smallest $d_i$.

14. The method according to claim 10, characterized in that a weight ($w_i$) is computed for each model trajectory as a measure for the correlation between the sensor output signal and the respective candidate output signal associated to the respective model trajectory, wherein particularly each weight ($w_i$) is a function of the difference between the sensor output signal and the respective candidate output signal, particularly the squared difference, wherein particularly for determining the spatial position of the tool within the object, a weighted average over corresponding points, particularly end points ($p_i$), of the model trajectories and/or over orientations ($o_i$) of the model trajectories is computed, wherein each of said points ($p_i$) and/or orientations ($o_i$) is weighted with the weight ($w_i$) associated to the model trajectory to which the respective point ($p_i$) and/or orientation ($o_i$) belongs.

15. A computer program product, which when executed on a computer is designed to conduct the following steps:
generating at least one candidate output signal based on a material property of an object along a model trajectory in a model of said object, the model trajectory being associated with at the least one candidate output signal,
receiving a sensor output signal depending on the material property along an actual trajectory in said object as an input,
determining a correlation between the sensor output signal and the at least one candidate output signal for determining the spatial position of the tool within the object.

* * * * *